United States Patent [19]

Sokol

[11] Patent Number: 6,069,167
[45] Date of Patent: *May 30, 2000

[54] USE OF ANTIOXIDANT AGENTS TO TREAT CHOLESTATIC LIVER DISEASE

[75] Inventor: Ronald J. Sokol, Denver, Colo.

[73] Assignee: University Technology Corporation, Boulder, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/784,247

[22] Filed: Jan. 15, 1997

Related U.S. Application Data

[60] Provisional application No. 60/010,049, Jan. 16, 1996.

[51] Int. Cl.$^7$ .......................... A01N 43/16; A01N 31/04; A01N 59/02
[52] U.S. Cl. ........................ 514/458; 514/725; 424/702
[58] Field of Search .................................... 514/458, 725; 424/702

[56] References Cited

U.S. PATENT DOCUMENTS

| | | | |
|---|---|---|---|
| 4,619,829 | 10/1986 | Motschan et al. | 424/128 |
| 5,326,757 | 7/1994 | Demopoulos | 514/167 |
| 5,332,579 | 7/1994 | Umbdenstock | 424/639 |
| 5,364,644 | 11/1994 | Walaszek et al. | 514/574 |

OTHER PUBLICATIONS

Sokol, Ronald J., et al. Evidence for Involvement of Oxygen Free Radicals in Bile Acid Toxicity to Isolated Rat Hepatocytes, *Hepatology* (1993)17:869–881.

Sokol, Ronald J., et al. Effect of Dietary Lipid Peroxidation and Hepatic Injury in the Bile Duct–Ligated Rat, *Journal of Lipid Research*(1991) 32:13491357.

Sokol,Ronald J., et al. Generation of Hydroperoxides in Isolated Rat Hepatocytes and Hepatic Mitochondria Exposed to Hydrophobic Bile Acids, *Gastroenterology* (1995) 109:1249–1256.

Sokol, Ronald J., et al. Multicenter Trial of d–a–Tocopheryl Polyethylene Glycol 1000 Succinate for Treatment of Vitamin E Deficiency in Children with Chronic Cholestasis, *Gastroenterology* (1993)104:1727–35.

Sokol, Ronald J., et al. Treatment of Vitamin E Deficiency During Chronic Childhood Cholestasis with Oral d–a–Tocopheryl Polyethylene Glycol–1000 Succiante, *Gastroenterology* (1987) 93:975–85.

Sokol, Ronald J., et al. Tocopheryl Polyethylene Glycol 1000 Succinate therapy for Vitamin E Deficiency During Chronic Childhood Cholestasis: Neurologic Outcome, *J. of Pediatrics* (1987) 3:830–836.

Sokol, Ronald J., et al. Improvement of Cyclosporin Absorption in Children after Liver Transplantation by Means of Water–Soluble Vitamin E, *The Lancet* (1991) 338:212–216.

Sokol, R.J., et al. Evidence of Free Radical Generation in Bile Acid Toxicity to Isolated Rat Hepatocytes, Abstract Amer. Assn. for the Study of Liver Diseases, Chicago, IL Oct. 31, 1992.

Sokol, Ronald J., et al. Free Radical Alteration of Hepatic Mitochondrial Lipids in End–Stage Liver Disease, Abstract Amer. Pediatric Society, Society for Pediatric Research, 1993, Abstract 25524.

Sokol, R.J., et al. Taurochenodeoxycholic acid Hepatotoxicity is Associated with Hepatocyte Hydroperoxide Generation and Mitochondrial Lipid Peroxidation, Abstract Joint Meeting of North Amer. Society for Pediatric Gastroenterology and Nutrition and the European Society for Paediatric Gastroenterology and Nutrition, Houston, TX, Oct. 10, 1994.

Sokol, R.J., et al. Vitamin E Reduces Oxidant Injury to Hepatic Mitochondria Caused by Intravenous Taurochenodeoxycholic Acid in the Rat, Abstract Amer. Liver Foundation, Chicago, IL Nov. 11, 1994.

Goff, M.C., et al. Mitochondrial Lipid Peroxidation Accompanies Intravenous Taurochenodeoxycholic Acid–Induced Hepatic Injury in the Rat, Abstract Amer. Gastroenterological Assn., New Orleans, LA, May 15, 1994.

Winklhofer–Roob, B.M., et al. Increased Generation of Hydrogen Peroxide by Isolated Rat Hepatic Mitochondria Exposed to Chenodeoxycholic Acid, Abstract Amer. Assn. for the Study of Liver Diseases, Chicago, IL Nov. 11, 1994.

Shivaram, K., et al. Idebenone Inhibits Taurochenodeoxycholic Acid Toxicity and Reduces Oxidant Stress in Isolated Rat Hepatocytes, Abstract Meetings of the AGA, AASLD at Digestive Disease Week, San Diego, CA May 14, 1995.

Winklhofer–Roob, B.M., et al. Dose–Dependent Increase in Hydrogen Peroxide Generation by Rat Hepatic Mitochondria Exposed to Chenodeoxycholic Acid and its Attenuation by Catalase, Abstract North Amer. Society for Pediatric Gastroenterology and Nutrition, Chicago, IL Nov. 3, 1995.

Database CAPLUS on STN, Abstract No. 1993:508953, Chen,H. et al., Protection by vitamin E, Selenium, and Beta–carotene Against Oxidative Damage in Rat Liver Slices and Homogenate, abstract Free Radical Bio. Med., 14(5), 1993.

Database WPIDS on STN, Abstract No. 95–044272, PLOCH, Capsule for Active Detoxification of Body Cells Contg. Vitamin E, Beta Carotene, Selenium and Zinc as Free Radical Scavengers, abstract, DE 4322070 A1 (Ploch E. M.) Jan. 12, 1995.

Database CAPLUS on STN, Abstract No. 1995:4707993, Chen, H. et al., Protection of Vitamin E, Selenium, Torlox C, Ascorbic Acid Palmitate, Acetylcysteine, Coenzyme Q0, Coenzyme Q10, Beta–carotene Canthaxanthin, and (+)–Catechin Against Oxidative Damage to Rat Blood and Tissues In Vivo, abstract, Free Radical Bio. Med., 18(5) 1995.

*Primary Examiner*—Theodore J. Criares
*Attorney, Agent, or Firm*—Sheridan Ross P.C.

[57] ABSTRACT

The present invention relates to formulations and methods for preventing and treating liver injury and fibrosis in cholestasis. This is accomplished by the administration of a composition which includes selected antioxidants.

8 Claims, No Drawings

USE OF ANTIOXIDANT AGENTS TO TREAT CHOLESTATIC LIVER DISEASE

This application claims the benefit of U.S. Provisional application Ser. No. 60/010,049, filed Jan. 16, 1996.

FIELD OF THE INVENTION

The present invention provides formulations and methods for preventing and treating liver injury and fibrosis that occur in cholestatic liver disease and related liver diseases. This is done by administering a composition that includes selected antioxidant compounds.

BACKGROUND OF THE INVENTION

Throughout this application, various publications are referred to by superscript Arabic numerals. Full bibliographic citations for these publications are set forth at the end of the application, immediately preceding the claims. The disclosures of these publications are hereby incorporated by reference.

Cholestatic liver diseases, or cholestasis, are a group of disorders of varying causes that result when bile flow is impaired. Cholestasis can cause progressive liver damage and eventually lead to end-stage liver disease. The mechanisms by which the liver is injured and fibrosis is stimulated in cholestatic liver disease are unclear.

Bile flow through the liver may be impaired at any point from the liver cell (hepatocyte) to the ampulla of Vater. For clinical purposes a distinction between intra and extrahepatic causes of cholestasis is helpful.

The most common intrahepatic causes of cholestasis in adults are viral or other hepatitis, drugs and alcoholic liver disease. Less common etiologies include primary biliary cirrhosis, primary sclerosing cholangitis, cholestasis of pregnancy, metastatic carcinoma, and numerous uncommon disorders. In addition, neonatal hepatitis, Alagille Syndrome, Byler's disease, Cystic Fibrosis and other familial cholestatic disorders are the most common intrahepatic forms in children.

Extrahepatic cholestasis is most often caused by a common bile duct stone or pancreatic carcinoma in adults. Less often, benign stricture of the common duct (usually related to prior surgery), ductal carcinoma, pancreatitis or pancreatic pseudocyst, and sclerosing cholangitis are causes. In children, extrahepatic biliary atresia, choledochal cyst, common bile duct stones or strictures and primary sclerosing cholangitis are the most common causes of extrahepatic cholestasis.

Cholestasis results from bile secretory failure; the mechanisms are complex, even in mechanical obstruction. Contributing factors include interference with microsomal hydroxylating enzymes with the attendant formation of poorly soluble bile acids; impaired activity of $Na^+$, $K^+$-ATPase, which is necessary for canalicular bile flow, altered membrane lipid composition and fluidity; interference with the function of microfilaments (thought to be important for canalicular function); and enhanced ductular reabsorption of bile constituents.

The pathophysiologic effects of cholestasis result from backup of bile constituents into the liver and the systemic circulation and their failure to enter the gut for excretion. Bilirubin, bile salts, and lipids are the most important constituents affected. Bilirubin retention produces mixed hyperbilirubinemia with spillover of conjugated pigment into the urine; stools are often pale because less bilirubin reaches the gut. Since bile salts are needed for absorption of fat and Vitamin K, impairment of biliary excretion of bile salts can produce steatorrhea and hypoprothrombinemia. If cholestasis is long-standing, concomitant calcium and Vitamin D malabsorption may eventually result in osteoporosis or osteomalacia. Vitamin A and Vitamin E malabsorption also occur in cholestasis, leading to clinical deficiency states for these vitamins. Cholesterol and phospholipid retention produce hyperlipidemia, though increased hepatic synthesis and decreased plasma esterification of cholesterol also contribute; triglyceride levels are largely unaffected. The lipids circulate as a unique, abnormal low-density lipoprotein called lipoprotein-X.

Jaundice, dark urine, pale stools, and generalized pruritus are the clinical hallmarks of cholestasis. Chronic cholestasis may produce muddy skin pigmentation, excoriations from pruritus, a bleeding diathesis, bone pain, and cutaneous lipid deposits (xanthelasma or xanthomas). These features are independent of the etiology. Any abdominal pain, systemic symptoms (e.g., anorexia, vomiting, fever), or additional physical signs reflect the underlying cause rather than cholestasis itself and therefore provide valuable etiologic clues.

Extrahepatic biliary obstruction usually requires intervention: surgery, endoscopic extraction of ductal stones, or insertion of stents and drainage catheters for strictures (often malignant) or partially obstructed areas. For nonoperable malignant obstruction, palliative biliary drainage can usually be attained via transhepatically or endoscopically placed stents. Endoscopic papillotomy with stone extraction has now largely replaced laparotomy in patients with retained common duct stones. For selected large ductal stones, biliary lithotripsy may be necessary to assist extraction of the fragments; sometimes they pass spontaneously.

Laparotomy is contraindicated in intrahepatic cholestasis; treating the underlying cause may suffice. Pruritus in irreversible disorders (e.g., primary biliary cirrhosis) usually responds to cholestyramine, which binds bile salts in the intestine. Unless severe hepatocellular damage is present, hypoprothrombinemia usually improves after phytonadione (Vitamin K1) therapy. Supplements of calcium and Vitamin D are often given in cases of long-standing irreversible cholestasis, but their impact on retarding metabolic bone disease is negligible. Vitamin A and water-soluble Vitamin E supplements will prevent deficiency of these fat-soluble vitamins, and severe steatorrhea can be minimized by partial replacement of dietary fat with medium-chain triglycerides.

However, chronic cholestatic liver diseases (including primary biliary cirrhosis, primary sclerosing cholangitis, extrahepatic biliary atresia, idiopathic neonatal hepatitis, Byler's disease, and arteriohepatic dysplasia) are a common cause of morbidity (and previously of mortality) and a leading indication for liver transplantation in children and adults.[1,2] Current treatment for cholestatic disorders centers on increasing bile flow (1) to reduce pruritus and hypercholesterolemia, (2) to improve intestinal absorption of dietary lipid and fat-soluble vitamins, and (3) theoretically, to reduce the accumulation of hepatotoxic substances (e.g., bile acids) and retard progression to portal fibrosis, cirrhosis, and end-stage liver disease.[3,4] The most promising therapy in this regard is the use of ursodeoxycholic acid,[3–6] a hydrophilic bile acid that has hepatoprotective as well as choleretic effects.[7,8] However, it is unclear whether current therapies are effective in significantly altering the overall progressive course of cholestatic disorders and resulting liver injury and the need for liver transplantation.

Development of new therapies for chronic cholestasis must be based on the underlying cellular and molecular events by which cholestasis causes liver damage.

Although many pathological processes may result in cholestasis as discussed above (e.g., structural, immunologic, genetic, and inflammatory), one of the postulated final common pathways leading to cholestatic liver injury is the intracellular accumulation of hydrophobic (toxic) bile acids.[9–12] The present inventor has previously suggested that oxidant stress may play a role in cholestatic hepatic injury[13] and that hydrophobic bile acids may be capable of initiating the generation of free radicals in the hepatocyte.[14] Support for this hypothesis was obtained in a bile duct-ligated rat model of cholestasis in which increased lipid peroxidation (oxidant damage) of hepatic mitochondria was correlated with the severity of cholestatic liver injury,[13] and in isolated rat hepatocytes exposed to bile acids.[14]

In summary, cholestatic liver disorders are a significant clinical problem in infants, children and adults[1,2,3]. Current medical therapies for cholestasis frequently fail to prevent the progression to cirrhosis and the other complications that occur in most patients. In 1993, approximately 270 adults and children underwent liver transplantation because of the complications of cholestatic disorders, at an estimated cost of over $40,000,000[23]. Thus, there is a considerable need for the development of new approaches to medical treatment of chronic cholestasis.

The present invention uses nutritional antioxidants to reduce free radical damage to the liver in clinical cholestasis, including alcoholic liver disease. Because low plasma levels of the three proposed antioxidants likely exist in persons with cholestasis, the invention provides moderately high doses of the antioxidants to correct any deficiencies and achieve above-normal blood levels of Vitamin E and beta carotene and higher than normal selenium levels. In a further aspect of the invention, antioxidant compositions are provided that can potentially aid recovery of injured hepatocytes so that these cells can generate endogenous antioxidants, particularly alpha-tocopherol. The solutions of the invention will be used to prevent and treat damage from cholestatic liver diseases of adults and children. The antioxidant compositions can reduce liver injury and thus slow down or prevent the progressive nature of cholestasis.

OBJECTS AND SUMMARY OF THE PRESENT INVENTION

It is an object of the present invention to provide safe, inexpensive, non-surgical methods for the prevention and treatment of liver injury that occurs in cholestasis.

It is also an object of the present invention to provide compositions which are ideally suited for this therapeutic goal.

It is a further object of the present invention to provide in vivo models of significant but reversible hepatic injury suitable for testing treatments of cholestasis.

Other objects of the present invention will be readily apparent to those of ordinary skill in the appropriate art.

In accordance with one aspect of the present invention, there is provided a method of preventing and treating liver damage caused by cholestasis in mammalian organisms, particularly human beings (together, hereafter referred to as "patients"), said method comprising the step of administering, in each 24-hour period, a formulation including the following compounds: water soluble Vitamin E, beta carotene, and selenium, each of said compounds of said formulation being present in an amount effective to prevent or treat liver injury that occurs in cholestasis, to patients in need of such treatment.

In accordance with another aspect of the present invention, there is provided the method of preventing and treating liver damage caused by cholestasis as previously described wherein the Vitamin E is provided in an amount of between about 25 and about 100 IU/kg/day; the beta carotene in an amount of between about 0.5 to 5.0 mg/kg/day; and the selenium about 1 to 5 micrograms/kg/day.

In a preferred embodiment in accordance with this aspect of the present invention, the formulation is administered in one or two dosages per day.

In accordance with another aspect of the present invention, there is provided a method of preventing and treating liver injury that occurs in cholestasis in patients, said method comprising the step of administering, in each 24-hour period, a formulation which includes Vitamin E, beta carotene, and selenium, each of the compounds of the formulation being present in an amount effective to prevent and treat liver injury that occurs in cholestasis, to a patient in need of such treatment.

In a more preferred embodiment of the present invention, there is provided a method of preventing and treating liver injury that occurs in cholestasis in patients, said method comprising a step of administering, in each 24-hour period a composition having a formulation which provides to a patient in need thereof Vitamin E in an amount of between about 25 to about 100 IU/kg/day; beta carotene in an amount of between about 0.5 to 5.0 mg/kg/day; and selenium in an amount of between about 1 to about 5 micrograms/kg/day.

In a most preferred embodiment in accordance with this aspect of the present invention, there is provided a method as previously described where the formulation provides about 50 IU/kg of Vitamin E, about 0.5 mg/kg of beta carotene, and about 1.0 microgram/kg of selenium per day per patient.

It is also preferred, in accordance with this aspect of the present invention, that the formulation is administered in one or two dosages per day.

Vitamin E refers to any group of at least eight related fat-soluble compounds with similar biological anti-oxidant activity, particularly alpha-tocopherol, but also including other isomers of tocopherol and the related compound tocotrienol. According to the instant invention, the most preferred form of Vitamin E is water soluble D-alpha-tocopheryl polyethylene glycol-1000 succinate (Eastman Chemical Corporation, Kingsport, Tennessee); the most preferred form of beta carotene is natural source water-dispersible β-carotene (Henkel); and the most preferred form of selenium is sodium selenate (Ciba, Canada).

The aforementioned antioxidants, when provided to a patient in sufficient quantity in a 24-hour period, should aid in the prevention and treatment of liver injury caused by cholestasis. While not wishing to be bound by theory, it is believed that the presence of sufficient amounts of certain antioxidants will significantly reduce the formation of free radicals in the liver. Cholestasis causes the generation of free radicals in liver cells and Kupffer cells, resulting in significant injury to liver cells and the induction of fibrosis. It is further postulated that the presence of sufficient quantities of Vitamin E, beta carotene (which is a precursor of Vitamin A) and selenium inhibit the metabolic oxidative processes involved in the conversion of arachidonic acid in platelets and macrophage cells, thus resulting in the reduced formation of prostaglandins, and several cytokines. The combined effects of these processes, if not inhibited, lead to the hepatic injury and fibrosis of cholestasis, forming the theoretical basis for use of antioxidants as treatment.

While some of the aforementioned ingredients are available in common multi-vitamin supplements, they are not provided in the combinations or in the quantities believed to be necessary to provide for the treatment of cholestasis as disclosed herein nor are they likely to be administered in a pattern sufficient to maintain their levels in the body consistently through a 24-hour period. Furthermore, there has been, apparently, no suggestion as to the use of these ingredients in any form or combination to treat liver injury caused by cholestasis. Other forms of beta carotene can include water miscible beadlets (80% all trans and 20% cis isomer) as well as other natural forms. Other suitable forms of selenium can include sodium selenate, sodium selenite, selenomethionine, and selenium yeast.

In accordance with another aspect of the present invention, there is provided an advantageous composition which should be particularly effective for use in the treatment of liver injury resulting from cholestasis. The pharmaceutically active antioxidant containing composition includes the correct amounts such that the following amounts will be delivered to patients in need thereof: a formulation including Vitamin E, to deliver between about 50 to 100 IU/kg/day; beta carotene to deliver between about 0.5 and 5.0 mg/kg/day; and selenium about 1 to 5 micrograms/kg/day; said composition capable of being administered in a 24-hour period and said composition being effective in the treatment of cholestasis in a mammalian organism, particularly a human being, in need thereof The formulation will contain about 75 IU of D-alpha-tocopheryl polyethylene glycol-1000 succinate per ml, about 0.75 mg beta carotene per ml, and about 1.5 micrograms of selenium per ml, or the appropriate amount based on the amount to be delivered to the patient as determined by one skilled in the art.

In a preferred embodiment in accordance with this aspect of the present invention, the pharmaceutically active antioxidant containing composition previously described includes amounts such that the final amount delivered to the patient will be about 50 IU/kg/day of Vitamin E; about 0.5 mg/kg/day of said beta carotene; and about 1.0 microgram/kg/day of selenium.

In a most preferred aspect of the present invention, the aforementioned pharmaceutically active antioxidant containing composition has a formulation including amounts sufficient to deliver about 50 IU/kg/day of Vitamin E, wherein the Vitamin E is in a water soluble form called D-alpha-tocopheryl polyethylene glycol-1000 succinate, or TPGS; 0.5 mg/kg/day of said beta carotene; and about 1.0 microgram/kg/day of selenium. While not wishing to be bound by theory, it is believed that the TPGS will solubilize the beta carotene to allow its absorption. TPGS has been shown to form micelles in the absence of bile salts and can improve the intestinal absorption of other fat-soluble substances, such as cyclosporin[15] and Vitamin D[16], when bile flow is impaired. Thus, the water-insoluble beta carotene will have enhanced absorption from the intestine when solubilized in a solution of TPGS. Without this solubilization, beta carotene is very poorly absorbed in cholestasis.

The aforementioned compositions can be particularly useful in the prevention and treatment of liver injury of any etiology caused by cholestasis. They represent a balance of ingredients which serve not only to reduce the number of free radicals formed in the liver, but also to inhibit the metabolic oxidation of arachidonic acid. The more preferred formulations in accordance with the present invention also enhance the performance of the composition by transporting certain antioxidant ingredients in the formulation and by offering the formulation in a form suitable for long-term use. These compositions, when provided in sufficient dosage over a period of 24 hours, can be useful in the prevention and treatment of liver injury and fibrosis caused by cholestasis.

In a still further aspect of the invention, a convenient in vivo reversible hepatic injury model system is provided that allows for testing of potentially therapeutic compounds. Preferably the model animal is a rodent, particularly a rat. The animal is exposed to an injurious bile acid or a conjugate thereof by rapid intravenous infusion. In a preferred embodiment, the injurious bile acid is chenodeoxycholic acid, or most preferably, the injurious bile acid is a conjugate of chenodeoxycholic acid, particularly taurochenodeoxycholic acid (TCDC). Intravenous infusion occurs for preferably less than 10 minutes, most preferably approximately 1 to 2 minutes. In the model system of the instant invention, dosage regimes of the injurious bile acid or analog thereof are sufficient to induce reversible hepatic injury. For example, dosage of TCDC can be approximately 10 μmol/ TCDC per 100 gram body weight of the test animal.

DETAILED DESCRIPTION OF THE PREFERRED EMBODIMENT

It is preferred that the antioxidants of the present invention be provided in a form which is as nearly pure as possible. They should be present without noxious lubricants (sand, soaps, talc), fillers, colors, flavors, binders, dispersants or like adjuvants commonly employed as delivery excipients in the pharmaceutical industry. The antioxidant ingredients, as well as other ingredients in the formulation, may be administered individually, or in combination, in a pill or capsule form, in powdered form or in the form of a solution, slurry or dispersion. However, for convenience, and dosage consistency, as well as for assisting in the uniform administration of various dosages of the individual ingredients throughout a 24-hour period, it is advantageous and preferred that the ingredients described herein be admixed and administered together in a solution to be taken orally once or twice per day. Further, it is most preferred that the formulation of the present invention be provided in the form of a solution to be taken orally.

The pharmaceutically active antioxidant containing compositions of the present invention have a formulation that includes Vitamin E, beta carotene and selenium. In a preferred embodiment of the present invention, there is provided a pharmaceutically active antioxidant containing composition which includes Vitamin E in an amount such that there is delivered to a patient between about 50 and 100 IU/kg/day; beta carotene in an amount of between about 0.5 and 5.0 mg/kg/day; and selenium in an amount of about 1 to 5 micrograms/kg/day, said composition capable of being administered in a single 24-hour period and said composition being effective in the treatment of liver injury resulting from cholestasis in patients.

It is important to note that these formulations are not meant as a replacement of those ingredients naturally produced in the body and/or consumed in the diet, but rather represent a supplement designed to increase normal blood levels.

Vitamin E (D-alpha tocopheryl polyethylene glycol-1000 succinate [TPGS] in the preferred embodiment) is broken down during digestion to yield alpha tocopherol which is the active antioxidant form. During cholestasis, poor bile flow makes the use of D-alpha tocopheryl polyethylene glycol-1000 succinate preferred because this form of Vitamin E is uniquely water-soluble and the only form of Vitamin E that is absorbed during severe cholestasis.[17,18,19] Unfortunately as a fat soluble vitamin, alpha tocopherol is probably not absorbed completely even in this form and a significant portion of the dosage ingested may be excreted. Thus, it is important that the amount of Vitamin E provided in each dosage be high enough to achieve the desired result. In general, alpha tocopherol and beta carotene enter cell membranes, including those of the mitochondria, and serve as lipoidal antioxidants scavenging hydroxyl, hydroperoxyl and other oxy radicals. The preferred form of Vitamin E, TPGS, is meant to aid in the ability of these two compounds to be absorbed by virtue of its solubilizing characteristics.

As is true with Vitamin E, the body's uptake of beta carotene is relatively slow and incomplete. Therefore the preferred Vitamin E form has been selected to solubilize the beta carotene to allow its absorption. Fortunately, to combat liver injury caused by cholestasis, the ideal administration regimen for beta carotene is similar to that of Vitamin E. Furthermore, there is an efficient regulatory system in the intestinal mucosa and the liver that prevents the overproduction of Vitamin A from its precursor, beta carotene. Thus, the bulk of the administered beta carotene remains unchanged and serves as a lipoidal antioxidant that scavenges hydroperoxyl and singlet oxygen. There is, therefore, little or no possibility of hypervitaminosis. In addition, the beta carotene aids in the suppression of the metabolic oxidation of arachidonic acid.

Selenium functions as an antioxidant because it is an essential component of the seleniun-dependent glutathione peroxidase, an enzyme that detoxifies lipid hydroperoxides and hydrogen peroxide. This enzyme is located intracellularly in the liver and also extracellularly around liver cells and in the circulating blood.[20] Additional selenoproteins may also have antioxidant properties.[21]

The combination of the three ingredients described previously, namely beta carotene, Vitamin E and selenium, are believed to provide for the prevention and/or treatment of liver injury and fibrosis in cholestasis. As previously described, it is believed that these ingredients help shut down the formation of free radicals and scavenge those free radicals that are produced.

The antioxidant solution can be formulated as follows: Pure TPGS (Eastman Chemical Company, Kingsport, Tenn.) in solid form is melted into a liquid state by heating to above 40° C. and stirring to ensure homogeneity. Weighed portions of the liquid TPGS are poured slowly into measured volumes of boiling sterile water, which are constantly stirred for 1 to 2 hours while cooling down to room temperature. Once at room temperature, to this 20% TPGS solution are added weighed portions of beta carotene and selenium while the mixture is stirred. The preferred form of beta carotene is natural source water dispersible P-carotene (Henkel) and of selenium is sodium selenate (Ciba, Canada). Alternatively, the beta carotene may be added to the TPGS while it is in its warmed, liquid state, then added to water, etc. The mixture is tested for shelf life, stability, and such tests well known to those skilled in the art.

Advantageously and preferably, the composition, in accordance with the present method is administered in one, or, if two, substantially equal dosages to a patient per day. Administration can be oral.

Other possible components of the antioxidant formulation of the instant invention can be coenzyme Q (ubiquinone)[22] and its derivatives or analogs at doses between about 0.5 mg/kg/day and 10 mg/kg/day. Without being bound by theory, the antioxidant properties of coenzyme Q are thought to derive from the ability of reduced coenzyme Q to react with ADP perferryl ions[38], and to directly react with lipid peroxide free radicals or with lipid free radicals[39]. Alternatively, coenzyme Q and its analogs or derivatives may function directly as electron or free radical scavengers.

The antioxidant formulations of the instant invention can optionally contain reducing agents. Such reducing agents can be any suitable reducing agent that maintains components in reduced state. Such reducing agents include, for example, succinate, glutamate and glutathione.

The instant invention also provides for an in vivo reversible hepatic injury model animal model, preferably a rodent model, most preferably a rat model. The animal can be dosed with any injurious bile acid or analogs thereof Suitable injurious bile acids include conjugates of chenodeoxycholic acid and lithocholic acid. A particularly suitable injurious bile acid analog is taurochenodeoxycholic acid. The injurious bile acid or analog can be administered by any suitable means, such as injection, oral or rectal administration. The injurious bile acid or analog thereof can be conveniently administered intravenously, particularly intravenous administration in the tail vein. The time of administration should be for less than 10 minutes, preferably approximately 1 to 2 minutes.

Hepatocyte swelling and a mild degree of cellular necrosis are the predominant histological findings of the in vivo model of the present invention. These histological findings are similar to those reported in a recently described rat model of continuous jugular vein infusion of TCDC at a rate of 0.4 to 0.6 $\mu$mol/min/100 gram over 60 minutes[31]. In both models, a significant degree of hepatocyte injury was demonstrated either by liver histology, elevated biliary excretion of lactate dehydrogenase (LDH) or elevated serum aspartate aminotransferase (AST), alanine aminotransferase (ALT) and bile acid concentrations. In addition, the continuous TCDC infusion model produced a marked reduction in bile flow and of hepatic bile secretion[31], confirming a cholestatic process. However, the model of the instant invention produced similar results at half the TCDC dosages of the continuous TCDC infusion model, and allows for rapid, convenient infusion of TCDC.

Importantly, in the in vivo model of the instant invention, the CDC concentrations were elevated to a similar extent as the other bile acids, indicating that the dose of TCDC had been cleared by the liver and that a cholestatic hepatic insult had occurred. In addition, the lack of substantial elevation of lithocholate conjugates indicated that conversion of CDC to lithocholic acid was not playing a major role. Histology of the liver at 4 hours after the 10 $\mu$mol/100 gram weight dose of TCDC showed mild hepatocyte swelling, variable necrosis of individual hepatocytes, mild portal tract infiltration with lymphocytes without bile duct injury, and accumulation of smooth eosinophilic globules. Based on these biochemical and histological findings, a suitable time point for the embodiment of the instant invention using TCDC as the toxic bile acid was the 4 hour, 10 $\mu$mol/100 gram weight dose. This represented a time and dosage of significant but reversible injury to hepatocytes that was much reduced by 24 hours after injection.

Test System: Isolated Hepatocytes

Adult male Sprague Dawley rats (250–275 grams body weight) were obtained from Sasco, Inc. (Omaha, Nebr.).

They were maintained on Purina lab chow (Ralston Purina Co., Chicago, Ill.) for 2–3 weeks and housed in polyethylene cages with stainless steel tops on a 24 hour light-dark cycle. All rats received humane care in compliance with the guidelines of the Committee on Laboratory Animal Research of the University of Colorado Health Sciences Center. Hepatocytes were isolated using a collagenase reperfusion technique that was a modification[24] of the method of Berry and Friend[25]. After administration of intraperitoneal anesthesia (50 mg/kg body weight), each rat liver was perfused in situ via the portal vein with Krebs-Henseleit buffer containing a mixture of 17 amino acids as previously described[24] under a 9% $O_2$/5% $CO_2$/86% $N_2$ atmosphere until perfusate was blood free (after approximately 25–50 ml of perfusate infusion). This was followed by perfusion for 10 minutes with 0.05% freshly prepared collagenase type II (Worthington Biochemical, Freehold, N.J.) solution in the same buffer at the same oxygen tension. The liver was then excised, the liver capsule was removed and cells dispersed by gentle agitation in media and then filtered through four layers of 4 inch×4 inch standard gauze. The resulting cell suspension was pelleted for 1 minute at 40 g and resuspended in Krebs-Henseleit buffer containing 0.5% glucose, 2% bovine serum albumin (BSA—fraction V; Cal Biochem, La Jolla, Calif.) and a mixture of 17 amino acids in a modified Krebs-Henseleit buffer, washed three times, and then resuspended to a final concentration of $1 \times 10^6$ cells/ml and used immediately. Initial cell viability measured by the trypan blue exclusion method[43] was above 95%. For all experimental procedures using the isolated hepatocyte preparation, 10 ml of the final cell suspension were placed into 25 ml sealed Erlenmeyer flasks under a 9% $O_2$/ 5% $CO_2$/86% $N_2$ atmosphere at 37° C. in a rotary water bath. This atmosphere was maintained throughout all experimental protocols with these cells by sparging every 15 minutes and after each entry into the flasks. Sparging was accomplished by sparging the Erlenmeyer flasks through rubber stoppers fitted with 3-way valves.

Determination of bile acid concentrations in hepatocytes

Approximately $2 \times 10^6$ hepatocytes were removed at appropriate time points, washed rapidly with ice-cold Krebs Hanseleit buffer and centrifuged at 40 g×1 minute three times (only the initial wash contained 2% BSA to remove adherent bile acids) and then stored at −70° C. For determination of baseline values of bile acids in normal rat hepatocytes, hepatocytes were isolated from normal rats according to Example 1, however the buffers used were albumin-free to prevent loss of hepatocellular bile acids during the isolation procedure. Free and conjugated bile acids were then measured by gas chromatography—mass spectrometry by modification of previously described techniques[30]. Briefly an internal standard (7-alpha, 12-alpha, hydroxy-5 beta cholanic acid) in butanol was added to each sample. The samples and appropriate standards where incubated with 2N sodium hydroxide at 80° C.×1.5 hour, cooled to room temperature, pH adjusted to 8.0 and trypsinized at 37° C. for 2 hours. Cooled samples were then eluted through C18 Sep-paks (Waters Corp., Milford, Mass.) using 85% methanol in water, the eluent was then evaporated using nitrogen gas in a 60° C. water bath. Conjugates were then hydrolyzed by fresh cholylglycine hydrolase at 37° C. overnight Free bile acids were then extracted in diethyl ether after acidification, followed by methylation and the formation of trimethylsilyl ethers. The residue was extracted in hexane and injected into a Hewlett-Packard 5790 gas chromatograph (Hewlett-Packard Company, Wilmington, Del.) fitted with a flame ionization detector and equipped with a 30 meter DB-1 capillary column (J&W Scientific, Folsom, California) with internal diameter of 0.25 mm and a film thickness of 0.25 µm at 215–290° C. Selected ion monitoring was performed on a Hewlett-Packard 5790-A mass selective detector. Results were expressed as nmol of each bile acid per $10^6$ hepatocytes and per mg protein.

Lipid Peroxidation Measurement in Isolated Hepatocytes

Lipid peroxidation, a measure of oxidant damage to hepatocytes, was assessed by the thiobarbituric acid reacting substances (TBARS) method[44,45]. For the TBARS assay, 0.2 ml of cell suspension was added to 0.5 ml of tichloroacetic acid (10% wt/vol), and to this mixture was added 1.0 ml of 0.67% thiobarbituric acid. Following heating in a water bath to 100° C. for 15 minutes, absorbance at 532 nm was measured in the supernatant[33].

When used in isolated hepatocytes in this manner, TBARS correlates well with other measurements of oxidant injury[34].

Lactate Dehydrogenase Measurement in Isolated Hepatocytes

Hepatocyte injury was assessed by the percentage of total cellular lactate dehydrogenase (LDH) release into the buffer medium. LDH was analyzed by measuring the rate of decrease in absorbance at 340 nm during reduction of pyruvate using a diagnostic kit supplied by Sigma Diagnostics (St Louis, Mo.). To ensure that this assay was not affected by the presence of the TCDC used in the examples described below, interference determinations were performed as follows. Total hepatocyte LDH activity was determined on the cell lysate (by sonification) of $10 \times 10^6$ hepatocytes incubated for 4 hours with or without TCDC at 1000 µmol/L. The total LDH activity in the lysate was virtually identical (90–96 units) in all combinations of TCDC, indicating that TCDC did not affect the LDH assay.

Hepatic Mitochondria Isolation

Mitochondria were isolated from 10 grams of fresh liver from individual rats by a modification of a previously described method[27]. Briefly, the liver was gently homogenized in a loose-fitting Potter-Elvehjm homogenizer in buffer containing 225 mM mannitol, 70 mM sucrose, 3 mM $KH_2PO_4$, 2mM EDTA, 0.1% BSA, 5 mM $MgCl_2$ (pH 7.0), filtered through cheesecloth and centrifuged at 400g×10 minutes. The supernatant was centrifuged at 10,000g for 10 minutes. The supernatant was aspirated and the pellet resuspended and centrifuged at 10,000g for 10 minutes. The resulting mitochondrial pellet was resuspended in 15 ml of buffer, divided into three tubes and added to digitonin (Sigma Chemical Company, St Louis, Mo., 0.29 mg for each gram of original liver) on wet ice×20 minutes, in order to minimize any contamination by lysosomes[28]. The resulting mitochondrial preparation was washed two times in the original buffer and centrifuged at 10,000g for 10 minutes. Samples of the pellet were taken for enzyme marker analysis. Two more washes were then performed using a buffer containing 50 mM MOPS/100 mM KCI, yielding the final mitochondrial pellet.

To determine if the mitochondrial fractions were of similar purity and lack of contamination, organelle-specific marker enzyme activity was measured in each fraction isolated and the percentage recovery and enrichment of mitochondria was calculated After storage at −70° C., for less than 3 months liver homogenate and mitochondrial fractions were analyzed for marker enzymes specific to mitochondria (citrate synthase[27]) and lysosomes (N-acetyl glucoseaminidase[27]) and for protein[29]. Enrichment was calculated by dividing the specific activity of the organelle fraction by that of the original hepatic homogenate, and the percentage recovery was calculated by dividing the total activity of the organelle fraction by that of the homogenate, and are presented below (Table A).

TABLE A

| Group | Citrate Syn. Enrichment | Citrate Syn. % Recovery | N-acetyl glucose- aminidase Enrichment | N-acetyl glucose- aminidase % Recovery |
|---|---|---|---|---|
| Control/ Vehicle | 12.9 ± 0.9 | 100 ± 0 | 1.1 ± 0.2 | 11.2 ± 1.4 |
| Control/ TCDC | 8.2 ± 0.6 | 85.3 ± 5.8 | 1.2 ± 0.1 | 13.8 ± 1.6 |
| Vitamin E/ Vehicle | 12.0 ± 1.3 | 97.1 ± 2.9 | 1.1 ± 0.1 | 12.4 ± 1.3 |
| Vitamin E/ TCDC | 7.8 ± 0.9 | 77.0 ± 5.4 | 1.3 ± 0.2 | 14.8 ± 1.7 |

Measurement of Hydroxide Generation by Isolated Mitochondria

Generation of hydroperoxides by mitochondria was monitored by the conversion of dichlorofluorescin (DCF) to fluorescent dichlorofluorescein (DCFein)[32]. Hepatic mitochondria were isolated from 250–300 gram male Sprague-Dawley rats and then loaded with 8 $\mu$mol/L of 2', 7'-dichlorofluorescin (DCF) diacetate (Eastman Fine Chemicals, Rochester, N.Y.), with minor modifications of the previously described procedure[24]. Briefly, the liver was removed under methoxyflurane anesthesia, rinsed and mitochondria were isolated by differential centrifugation. To remove residual lysosomes, mitochondria were incubated with digitonin as described in reference number 24. Purity of mitochondrial preparations was assessed by electron microscopy of selected mitochondrial pellets as described previously[26]. Microscopy showed intact mitochondrial structure and membranes and minimal contamination by any other membranous structures.

The final mitochondrial pellet was resuspended in buffer containing Tris (30 mmol/L), potassium chloride (150 mmol/L), magnesium chloride (5 mmol/L) and potassium phosphate (3 mmol/L) at pH 7, and then loaded with DCF-diacetate (8 $\mu$mol/L) at 37° C. for 30 minutes and washed twice with the same buffer, followed by centrifugation at 10,000 g for 10 minutes and final resuspension in 200 ml of the buffer. The final mitochondrial suspension was then incubated in 20 ml aliquots under room air at 37° C. for 90 minutes. Aliquots of mitochondria were removed every 15 minutes and DCFein fluorescence (490 nm excitation and 520 nm emission wavelengths) was recorded as a measure of hydroperoxide generation[24,32]. Results were expressed as picomoles of DCFein per mg mitochondrial protein present at a given time point and as the rate of DCFein generation per mg protein per minute. The average protein content of the final mitochondrial suspension, determined by the bicinchoninic acid protein assay (Sigma Chemical Company, St. Louis, Mo.) was 0.24 mg per ml.

Measurement of Lipid Peroxidation by Isolated Mitochondria

Fresh mitochondria were analyzed for lipid peroxidation as an index of oxidant damage by the lipid-conjugated diene method of Recknagel and Ghoshal[35] with the modification of Bacon et al[36]. Briefly, lipids were extracted from mitochondria pellets with chloroform and methanol (2:1, vol/vol), and the lipid in chloroform was dried under a stream of oxygen-free nitrogen[27]. The dried lipid was redissolved in 1.5 ml of spectrophotometric grade cyclohexane. Absorbance from 220 to 275 nm was recorded against a cyclohexane blank on a Lambda 2 UV/is Spectrometer (Perkin-Elmer Corp., Norwalk, Conn.). Lipid concentration was approximately 0.5 mg/mi of cyclohexane. After the UV measurements, a 250 $\mu$l aliquot from each sample was analyzed for total lipid content by the method of Chiang et al.[37], and absorbance measurements were normalized to a denominator of 1.0 mg lipid per ml of cyclohexane. Lipid peroxidation was estimated by calculating the difference in absorption at 233 nm (the peak absorbance for conjugated dienes) between each rat and the mean of the values from control rats.

EXAMPLE 1

Test System: in vivo Reversible Hepatic Injury Model

Young adult male Sprague-Dawley rats (150–180 gram weight) purchased from Sasco, Inc. (Omaha, Nebr.) were fed Purina Lab Chow (Ralston Purina Co., Chicago, Ill.) ad libitum for 2–3 weeks and housed in polyethylene cages with stainless steel tops on a 12-hour light-dark cycle. All rats received humane care in compliance with the guidelines of the Animal Use in Research Committee of the University of Colorado Health Sciences Center. Rats were then randomly assigned (4–5 per group) to receive 0 (vehicle only), 5, 10, or 20 $\mu$mol of taurochenodeoxycholic acid (TCDC)/ 100 gram body weight. TCDC is a conjugate of the bile acid most implicated in cholestatic liver injury9,11,12. TCDC was solubilized in 5% dextrose, 10% BSA, and 0.45% normal saline. TCDC was administered while rats were under light methoxyflurane anesthesia as an intravenous bolus of the desired dose in 1 to 2 minutes through the tail vein. TCDC dosing was performed between 7 and 9 am. Rats recovered from the injection uneventfully and blood was obtained at 0, 4, 8, 12 and 24 hours after the injection for determination of AST, ALT total bilirubin and alkaline phosphatase by an automated chemical analyzer (Hitachi 747 Chemical Analyzer).

Intravenous bolus injections of TCDC in rats caused a significant rise in serum AST and ALT concentrations in a dose-dependent manner (Table 1), with peak values attained 4 hours after injection. There were no significant changes in serum alkaline phosphate or total serum bilirubin concentrations in response to TCDC (data not shown).

TABLE 1

Dose Response of Intravenous Taurochenodeoxycholic acid (TCDC) and Hepatic Toxicity.

| Hours after IV | | Dose of Intravenous TCDC ($\mu$Mol/Kg Body Weight) | | | |
|---|---|---|---|---|---|
| TCDC dose | | 0 (n = 4) | 5 (n = 4) | 10 (n = 4) | 20 (n = 4) |
| 0 | AST* | 61 ± 1 | 73 ± 9 | 92 ± 8 | 70 ± 6 |
| | ALT* | 54 ± 5 | 52 ± 6 | 53 ± 3 | 64 ± 9 |
| 4 | AST | 66 ± 6 | 121 ± 24 | 3679 ± 1105 | 1456 ± 748 |
| | ALT | 51 ± 8 | 92 ± 23 | 1855 ± 701 | 1712 ± 554 |
| 8 | AST | 59 ± 14 | 110 ± 12 | 2233 ± 1906 | 2057 ± 939 |

TABLE 1-continued

Dose Response of Intravenous Taurochenodeoxycholic acid (TCDC) and Hepatic Toxicity.

| Hours after IV | | Dose of Intravenous TCDC ($\mu$Mol/Kg Body Weight) | | | |
|---|---|---|---|---|---|
| TCDC dose | | 0 (n = 4) | 5 (n = 4) | 10 (n = 4) | 20 (n = 4) |
|  | ALT | 56 ± 10 | 88 ± 12 | 1963 ± 701 | 1238 ± 257 |
| 12 | AST | 78 ± 10 | 105 ± 12 | 605 ± 249 | 1282 ± 375 |
|  | ALT | 66 ± 11 | 70 ± 7 | 492 ± 291 | 851 ± 167 |
| 24 | AST | 85 ± 3 | 89 ± 3.5 | 328 ± 82 | 399 ± 41 |
|  | ALT | 81 ± 6 | 72 ± 7 | 198 ± 82 | 362 ± 75 |

*Values expressed as IU/L
All values are mean ± SEM

Because serum AST and ALT concentrations peaked at 4 hours, further evaluation of liver injury was performed at that time point Total concentrations (conjugated+free bile acids) of individual bile acids were measured in serum obtained at 4 hours by gas chromatography-mass spectroscopy (GC-MS), as previously described[30]. Briefly, after serum samples were extracted with the addition of the internal standard 7-alpha, 12-alpha, dihydroxy-5 beta cholanic acid, trimethylsilyl esterification was performed. Individual bile acids were then quantified by GC or GC-MS using a Hewlett-Packard 5790 flame ionization detector equipped with a 30 meter DB-1 capillary column with internal diameter of 0.25 mm and a film thickness of 0.25 micrometers (J & W Scientific, Folsom, Calif.). For GC-MS measurements, a Hewlett-Packard 5970-A mass selective detector operating in selective ion monitoring mode was used. Results were expressed as $\mu$mol/L for each individual bile acid. Analysis of serum for concentrations of individual bile acids obtained 4 hours after the intravenous injections showed significant increases in most bile acids in the TCDC (10 $\mu$mol/100 gram dose) group compared to the vehicle-injected rats (Table 2). In addition, hepatic mitochondria isolated (according to Example 5) 4 hours after treatment with 10 $\mu$mol TCDC/100 gram showed significant elevations of lipid-conjugated dienes relative to rats treated with vehicle only. This indicated that in vivo TCDC toxicity was accompanied by mitochondrial oxidant injury.

TABLE 2

Serum Bile Acid Concentrations ($\mu$mol/L)
Four Hours after Intravenous TCDC Dose

| | Experimental Group | |
|---|---|---|
| | TCDC (n = 5) | Vehicle (n = 4) |
| Lithocholic acid | 0.6 ± 0.2 | 0 |
| Deoxycholic acid | 4.8 ± 1.2 | 4.0 ± 1.2 |
| alpha-Muricholic acid | *77.4 ± 15.9 | 7.2 ± 5.2 |
| beta-Muricholic acid | *12.4 ± 3.3 | 1.0 ± 0.7 |
| Chenodeoxycholic acid | *23.2 ± 2.6 | 7.2 ± 0.6 |
| Cholic acid | *134.8 ± 30.2 | 24.2 ± 4.1 |
| Ursodeoxycholic acid | 4.4 ± 0.4 | 2.5 ± 0.3 |
| Total Bile Adds | *277.8 ± 49.0 | 53.8 ± 5.1 |

All values expressed as mean ± SEM of $\mu$mol/L of total concentration (conjugates plus unconjugates) of individual serum bile acids.
*P < 0.05 versus vehicle group by t-test

EXAMPLE 2

Effect of Vitamin E on Oxidant Injury Produced by Intravenous TCDC

Rats were divided into two treatment groups. One group was pretreated with parenteral Vitamin E (all-rac-alpha tocopherol, Ephynal, Hoffmann-LaRoche, Nutley, N.J.). The other group was not pretreated. These rats then received either vehicle or TCDC (10 $\mu$mol/100 $\mu$m body weight) by tail vein injection (as described in Example 1). After 2 weeks of receiving lab chow ad libitum, rats were randomly assigned to treatment with either (a) 3 mg/100 gram body weight parenteral vitamin E (all-rac-alpha tocopherol) by intraperitoneal injection (i.p.) administered every other day for a total of 5 doses plus an identical intravenous dose immediately prior to the intravenous TCDC injection or (b) administration of an equivalent volume of normal saline (control) given by the same route and schedule as the vitamin E. All i.p. injections were administered under light methoxyflurane anesthesia. Following the vitamin E or saline injections, rats were randomly assigned to receive a tail vein bolus injection of either TCDC or vehicle. Rats were sacrificed four hours later and serum was analyzed for AST, ALT, total bilirubin and alkaline phosphatase. Serum alpha tocopherol levels were measured using high performance liquid chromatography (HPLC) with absorbance detection[40]. The serum alpha tocopherol:total lipids ratio (mg/gm) was calculated as an additional index of vitamin E status[41].

The liver was rapidly removed at sacrifice, the hepatic mitochondria were isolated as set forth above and analyzed for lipid-conjugated dienes as described above. A specimen of liver was also immediately frozen, protected from light and stored at −70° C. and subsequently analyzed for alpha tocopherol and reduced ubiquinol-9 by HPLC with electrochemical detection[42]. The results were expressed as nmol alpha tocopherol or nmol reduced ubiquinol-9 per gram wet weight of liver.

Parenteral vitamin E treatment led to significant increases in serum vitamin E concentrations, serum vitamin E:total lipid ratios, and hepatic alpha tocopherol concentrations in rats receiving either TCDC or vehicle (Table 3). Hepatic reduced ubiquinol-9 was similar in all four treatment groups. Pretreatment with parenteral vitamin E resulted in a significant decrease (approximately 70%) in serum AST and ALT concentrations in rats receiving TCDC infusion (Table 3). There was no effect on these values in rats receiving intravenous vehicle, nor on alkaline phosphatase or serum bilirubin concentrations in any group (data not shown). Pretreatment with vitamin E resulted in a significant reduction in mitochondrial lipid-conjugated dienes in the i.v. TCDC group, accompanying the reduction in AST and ALT. There were significant correlations between mitochondrial lipid-conjugated diene values and concentrations of serum AST (r=0.59, p=0.0004 and ALT (r=0.55, p=0.002). No changes in hepatic ubquinol-9 concentrations were observed in relation to TCDC or vitamin E treatment Therefore, pretreatment with vitamin E attenuated both the hepatic injury and the severity of mitochondrial lipid peroxidation.

TABLE 3

Effect of Vitamin E Treatment on TCDC Hepatic Toxicity

| | Control/ Vehicle (n = 8) | Control/ TCDC (n = 13) | Vitamin E/ Vehicle (n = 7) | Vitamin E/ TCDC (n = 12) |
|---|---|---|---|---|
| Serum alpha tocopherol (ug/ml) | [a]6.0 ± 0.2 | [a]5.5 ± 0.3 | [b]9.9 ± 0.7 | [b]13.2 ± 0.7 |
| Serum alpha tocopherol/ total lipids (mg/gm) | [a]2.04 ± 0.06 | [a]1.47 ± 0.13 | [b]3.71 ± 0.20 | [b]4.41 ± 0.5 |
| Hepatic alpha tocopherol (nmol/gm liver) | [a]34.0 ± 7.4 | [a]35.5 ± 7.4 | [b]84.4 ± 11.2 | [b]167.4 ± 28.8 |
| Hepatic reduced ubiquinol-9 (nmol/gm liver) | [a]72.8 ± 5.3 | [a]72.3 ± 6.0 | [a]67.7 ± 4.7 | 71.9 ± 5.2 |
| AST (IU/L) | [a]85 ± 5 | [b]2472 ± 505 | [a]81 ± 2 | [c]870 ± 278 |
| ALT (IU/L) | [a]74 ± 3 | [b]1111 ± 213 | [a]61 ± 5 | [c]325 ± 78 |
| Bilirubin (mg/dL) | 0.2 ± 0.02 | 0.4 ± 0.1 | 0.2 ± 0.02 | 0.2 ± 0.02 |
| Lipid-conjugated dienes (delta abs. 233 nm/mg lipid) | [a]0.00 ± 0.02 | [b]0.24 ± 0.02 | [a]−0.03 ± 0.02 | [c]0.13 ± 0.01 |

*Values in each row with different superscript letters are significantly different from each other ($p < 0.05$) by ANOVA.

References

1. Whitington PF, Balistreri WF, Liver transplantation in pediatrics: indications, contraindications, and pretransplant management. J Pediatr 1991; 118:169–177.
2. Starzl TE, Demetris AJ, Van Thiel D. Liver transplantation. N Engl J Med 1989; 321:1014–1022.
3. Ramirez RO, Sokol RJ. Medical management of cholestasis. In: Suchy FJ, ed. Liver disease in children. St. Louis, Mo.: Mosby, 1994:356–388.
4. Fallon MB, Anderson JM, Boyer JL. Intrahepatic cholestasis. In: SchiffL, Schiff ER, eds. Diseases of the liver. 7th ed. Philadelphia: Lippincolt 1993:343–361.
5. Lindor KD, Dickson ER, Baldus WP, Jorgensen RA, Ludwig J, Murtaugh PA, Harrison JM, Weisner RH, Anderson ML, Lange SM, Lesage G, Rossi SS, Hofmann AF. Ursodeoxycholic acid in the treatment of primary biliary cirrhosis. Gastroenterology 1994; 106:1284–1290.
6. OBrien CB, Senior JR, Agora-Mirchandani R, Batta AK, Salen G. Ursodeoxycholic acid for the treatment of primary sclerosing cholangitis: a 30-month pilot study. Hepatology 1991; 14:838–847.
7. Galle PR, Theilmann L, Raedsch R, Otto G, Stiehl. Ursodeoxycholate reduces hepatoxicity of bile salts in primary human hepatocytes. Hepatology 1990; 12:486–491.
8. Heuman DM, Pandak WM, Hylemon PB, Vlahcevic ZR. Conjugates of Ursodeoxycholate protect against cytotoxicity of more hydrophobic bile salts: in vitro studies in rat hepatocytes and human erythrocytes. Hepatology 1991; 14:920–926.
9. Greim H, Czygan P, Schaffner F, Popper H. Determination of bile acids in needle biopsies of human liver. Biochem Med 1973; 8:280–286.
10. Festi D, Labate AMM, Roda A, Bazzoli F, Frabboni R, Rucci P, Taroni F, Aldini R, Roda E, Barbara L. Diagnostic effectiveness of serum bile acids in liver diseases as evaluated by multi variate statistical methods. Hepatology 1983;3:707–713.
11. Hofmann AF, Popper H. Ursodeoxycholic acid for primary biliary cirrhosis. Lancet 1987;2:398–399.
12. Attili AF, Angelico M, Cantafora A, Alvaro D, Capocaccia L. Bile acid-induced liver toxicity: relation to the hydrophobic-hydrophilic balance of bile acids. Med Hypotheses 1986;19:57–69.
13. Sokol RJ, Devereaux M, Khandwala R. Effect of dietary lipid and Vitamin E on mitochondrial lipid peroxidation and hepatic injury in the bile duct-ligated rat. J Lipid Res 1991; 32:1349–1357.
14. Sokol RJ, Devereaux M, Khandwala R, O'Brien K. Evidence for involvement of oxygen free radicals in bile acid toxicity to isolated rat hepatocytes. Hepatology 1993;17:869–881.
15. Sokol RJ, Johnson KE, Karrer FM, Narkewicz MR, Smith D, Kam I. Improvement of cyclosporin absorption in children after liver transplantation by means of water soluble Vitamin E. Lancet 1991; 338:212–215.
16. Argao EA, Heubi JE, Hollis BW, Tsang RC. D-alpha-tocopheryl polyethylene glycol-1000 succinate enhances the absorption of Vitamin D in chronic cholestatic liver disease in infancy and childhood. Pediatr Res 1992; 31:146–150.
17. Sokol, RJ, Heubi JE, Butler-Simon N, McClung HJ, Lilly JR, Silverman A. Treatment of Vitamin E deficiency during chronic childhood cholestasis with oral D-alpha tocopheryl polyethylene glycol-1000 succinate. Gastroenterology 1987; 93:975–985.
18. Sokol RJ, Butler-Simon NA, Bettis D, Smith D, Silverman A. Tocopheryl polyethylene glycol-1000 succinate therapy for Vitamin E deficiency during childhood cholestasis: neurologic outcome. J. Pediatr 1987; 111:830–836.
19. Sokol RJ, Butler-Simon N, Conner C, Heubi JE, Sinatra F, Suchy F, Heyman MB, Perrault J, Rothbaum RJ, Levy J, Iannaccone ST, Schneider B, Rosenblum JL, Koch T, Narkewicz MR. Multicenter trial of D-alpha tocopheryl polyethylene glycol-1000 succinate for treatment of Vitamin E deficiency in children with chronic cholestatic liver disease. Gastroenterology 1993; 10x: 1727–1735.
20. Rotruck JT, Pope AL, Ganther HE, et al. Selenium: biochemical role as a component of glutathione peroxidase. Science 1973; 179:588–590.

21. Burk RF. Recent development in trace elements metabolism and function: newer roles of selenium in nutrition. J. Nutr. 1989; 199:1051–1054.

22. Stocker R. Bowry VW, Frei B. Ubiquinol-10 protects human low density lipoprotein more efficiently against lipid peroxidation than does D-tocopheryl. Proc Natl Acad Sci USA 1991; 88:1646–1650.

23. UNOS Update 1995; 11:37–41.

24. Sokol RJ, Winklhofer-Roob BM, McKim JM Jr., Devereaux MW: Generation of hydroperoxides in isolated rat hepatocytes and hepatic mitochondria exposed to hydrophobic bile acids. Gastroenterology 1995; 109: 1249–1256.

25. Berry MN, Friend DS. High yield preparation of isolated rat parenchymal cells. J. Cell Biol. 1969; 506–520.

26. Sokol RJ, Devereaux MW, Mierau GW, Hambidge KM, Shikes RH. Oxidant injury to hepatic mitochondrial lipids in rats with dietary copper overload. Modification by vitamin E deficiency. Gastroenterology 1990; 99: 1061–1071.

27. Sokol RJ, Devereaux MW, O'Brien K, Khandwala RA, Loehr JP. Abnormal hepatic mitochondrial respiration and cytochrome C oxidase activity in rats with long term copper overload. Gastroenterology 1993; 105: 178–187.

28. Lowenstein J, Scholte HR, Wit-Peeter EM. A rapid and simple procedure to deplete rat liver mitochondria of lysosomal activity. Biochim. Biophys. Acta 1970; 223: 432–436.

29. Lowry OH, Rosebrough NJ, Farr AL, Randall RJ. Protein measurement with folin phenol reagent. J. Biol. Chem. 1951; 193: 265–275.

30. Everson GT, Daggy BP, McKinley C, Story JA. Effects of psyllium hydrophilic mucilloid on LDL-cholesterol and bile acid synthesis in hypercholesterolemic man. J. Lipid Res. 1992; 1183–1192.

31. Schumucker DL, Ohta M., Kanai S, Sato Y, Kitani K Hepatic injury induced by bile salts: Correlation between biochemical and morphological events. Hepatology 1990; 12: 1216–1221.

32. Cathcart R, Schwiers E, Ames BN. Detection of picomole levels of hydroperoxides using a fluorescent dichlorofluorescein assay. Anal. Biochem. 1983; 143: 111–116.

33. Combettes L, Dumont M, Berthon B, Erlinger S, Claret M. Release of calcium from the endoplasmic reticulum by bile acids in rat liver cells. Jour. Biol. Chem. 1988; 263: 229–2303.

34. Smith MT, Thor H, Hartzell P, Orrenius S. The measurement of lipid peroxidation in isolated hepatocytes. Biochem. Pharmacol. 1982; 3: 19–26.

35. Recknagel RO, Ghoshal AK Quantitative estimation of peroxidative decomposition of rat liver microsomal and mitochondrial lipids after carbon tetrachloride poisoning. Exp. Mol. Pathol. 1965; 5: 413–426.

36. Bacon BR, Tavill AS, Brittenham GM, Park CH, Recknagel RO. Hepatic lipid peroxidation in vivo in rats with chronic iron overload. J. Clin. Invest 1983; 71: 429–439.

37. Chiang SP, Gessert CF, Lowry OH. Calorimetric determination of extracted lipids. Research Report 1957, 56–113. Air University School of Aviation Medicine, United States Air Force, Texas.

38. Svingen BA, Buerge JA, ONeal FO, Aust SD. The mechanism of NADPH-dependent lipid peroxidation. The propagation of lipid peroxidation. J. Biol. Chem. 1979; 254: 5892–5899.

39. Landi L, Cabrini L, Tadolini B, Sechi AM, Pasquali P. Incorporation of ubiquinones into lipid vesicles and inhibition of lipid peroxidation. Ital. J. Biochem. 1985; 34: 356–363.

40. Zoellner N. Kirsch K. A micromethod for lipids using a sulphooxanillin reaction. Z. GesamteExp. Med. 1961; 135: 545–561.

41. Sokol RJ, Heubi JE, lannaccone ST, Bove KE, Balistreri WF. Vitamin E deficiency with normal serum vitamin E concentrations in children with chronic cholestasis. N.Engl.J.Med. 1984; 310: 1209–1212.

42. Lang JK, Gohil K, Packer L. Simultaneous determination of tocopherols, ubiquinols, and ubiquinones in blood, plasma, tissue homogenates and subcelllular fractions. Anal. Biochem. 1986; 157: 106–116.

43. Baur H., et al. Criteria of viability of isolated liver cells. Physiol. Chem. 1975; 356:827–838.

44. Buege JA, Aust SD, Fmicrosomal lipid peroxidation. Methods Enzymol. 1978; 52:302–310.

45. Sokol RJ, et al. Copper toxicity and lipid peroxidation in isolated rat hepatocytes: effect of vitamin E. Pediatr. Res. 1989; 25: 55–62.

What is claimed is:

1. A pharmaceutically active antioxidant containing composition consisting essentially of a formulation to deliver to a patient Vitamin E in an amount between about 50 to about 100 IU/kg/day, beta carotene in an amount of between about 0.5 to 5.0 mg/kg/day, and selenium in an amount of about 1.0 to 5.0 micrograms/kg/day.

2. The pharmaceutically active antioxidant containing composition of claim 1, wherein said formulation delivers about 50 IU/kg/day of Vitamin E; about 0.5 mg/kg/day of beta carotene; and about 1.0 microgram/kg/day of selenium.

3. The pharmaceutically active antioxidant containing composition of claim 2, wherein said Vitamin E is D-alpha tocopheryl polyethylene glycol-1000 succinate.

4. A method of preventing and treating liver injury and fibrosis in cholestasis in mammalian organisms, said method comprising the step of administering a formulation including the compounds Vitamin E, beta carotene and selenium, each of said compounds of said formulation being present in an amount effective to treat cholestasis, to a mammalian organism in need of such treatment.

5. The method of preventing and treating liver injury and fibrosis in cholestasis of claim 4; wherein said Vitamin E is present in an amount sufficient to deliver to a patient about 50 IU/kg/day; said beta carotene in an amount of about 0.5 mg/kg/day, and said selenium in an amount of about 1.0 microgram/kg/day.

6. A pharmaceutically active composition comprising a formulation to deliver to a patient Vitamin E in an amount between about 50 to about 100 IU/kg/day, beta carotene in an amount of between about 0.5 to 5.0 mg/kg/day, and selenium in an amount of about 1.0 to 5.0 $\mu$g/kg/day.

7. The pharmaceutically active composition of claim 6, wherein the formulation delivers about 50 IU/kg/day of Vitamin E, about 0.5 mg/kg/day of beta carotene, and about 1.0 $\mu$g/kg/day of selenium.

8. The pharmaceutically active composition of claim 7, wherein said Vitamin E is D-alpha tocopheryl polyethylene glycol-1000 succinate.

* * * * *